(12) United States Patent
Katsuki et al.

(10) Patent No.: US 10,577,637 B2
(45) Date of Patent: Mar. 3, 2020

(54) ENZYME ELECTRODE

(71) Applicants: ARKRAY, Inc., Kyoto (JP); Ultizyme International Ltd., Tokyo (JP)

(72) Inventors: Koji Katsuki, Kyoto (JP); Hisashi Kaneda, Kyoto (JP); Junko Shimazaki, Tokyo (JP)

(73) Assignees: ARKRAY, Inc., Kyoto (JP); Ultizyme International Ltd., Tokyo (JP)

( * ) Notice: Subject to any disclaimer, the term of this patent is extended or adjusted under 35 U.S.C. 154(b) by 0 days.

(21) Appl. No.: 15/294,374

(22) Filed: Oct. 14, 2016

(65) Prior Publication Data

US 2017/0107555 A1 Apr. 20, 2017

(30) Foreign Application Priority Data

Oct. 15, 2015 (JP) ................. 2015-204033
Oct. 5, 2016 (JP) ................. 2016-196930

(51) Int. Cl.
*C12Q 1/00* (2006.01)
*G01N 27/327* (2006.01)
(Continued)

(52) U.S. Cl.
CPC ............. *C12Q 1/006* (2013.01); *C12Q 1/001* (2013.01); *C12Q 1/25* (2013.01); *C12Q 1/32* (2013.01); *C23C 14/0605* (2013.01); *C23C 14/205* (2013.01); *C23C 14/24* (2013.01); *C23C 14/34* (2013.01); *C23C 14/58* (2013.01); *C23C 16/06* (2013.01); *C23C 16/44* (2013.01); *C23C 16/56* (2013.01); *C23C 28/00* (2013.01); *G01N 27/3271* (2013.01); *G01N 27/3272* (2013.01)

(58) Field of Classification Search
CPC .. G01N 27/40; G01N 27/3272; G01N 27/327; G01N 27/48; G01N 27/26; C12Q 1/00; C12Q 1/02; C12Q 1/006; C12Q 1/34; C12Q 1/54; A61B 5/150274; A61B 5/05; A61B 5/14532
See application file for complete search history.

(56) References Cited

U.S. PATENT DOCUMENTS

2005/0067278 A1 3/2005 Sode
2008/0090278 A1* 4/2008 Kitabayashi ......... C12N 9/0006
435/188

(Continued)

FOREIGN PATENT DOCUMENTS

EP 2012121 A1 1/2009
EP 2447358 A1 5/2012
(Continued)

OTHER PUBLICATIONS

Okuda et al., Biosensors and Bioelectronics, 18, 2003, 699-704 (Year: 2003).*

(Continued)

*Primary Examiner* — Gurpreet Kaur
(74) *Attorney, Agent, or Firm* — Morgan, Lewis & Bockius LLP

(57) ABSTRACT

An enzyme electrode includes an electrode, and a detection layer which contacts the electrode and contains a crosslinking agent, an electrically conductive macromolecule and an enzyme transferring and receiving electrons to and from the electrode and does not contain an electron transfer subunit.

19 Claims, 4 Drawing Sheets

(51) Int. Cl.

| | | |
|---|---|---|
| *C12Q 1/32* | (2006.01) | |
| *C12Q 1/25* | (2006.01) | |
| *C23C 14/06* | (2006.01) | |
| *C23C 14/20* | (2006.01) | |
| *C23C 14/24* | (2006.01) | |
| *C23C 14/34* | (2006.01) | |
| *C23C 14/58* | (2006.01) | |
| *C23C 16/06* | (2006.01) | |
| *C23C 16/44* | (2006.01) | |
| *C23C 16/56* | (2006.01) | |
| *C23C 28/00* | (2006.01) | |

(56) References Cited

U.S. PATENT DOCUMENTS

| | | | | |
|---|---|---|---|---|
| 2012/0107903 A1* | 5/2012 | Sode | ............ | C12N 9/0006 435/188 |
| 2012/0273368 A1* | 11/2012 | Tsukada | ............ | C12Q 1/004 205/775 |
| 2015/0129425 A1* | 5/2015 | Tsukada | ............ | G01N 27/327 204/403.14 |
| 2015/0192537 A1* | 7/2015 | Sekimoto | ............ | G01N 27/327 204/403.14 |
| 2016/0177365 A1 | 6/2016 | Katsuki | | |

FOREIGN PATENT DOCUMENTS

| | | |
|---|---|---|
| EP | 3078965 A1 | 10/2016 |
| EP | 3086113 A1 | 10/2016 |
| JP | 2014-006154 A | 1/2014 |
| JP | 2014-006155 A | 1/2014 |
| WO | 2015/020149 A1 | 2/2015 |

OTHER PUBLICATIONS

Koopal et al., Biosensors&Bioelectronics, 1992, 7, 461-471 (Year: 1992).*
Extended European Search Report issued in corresponding European Patent Application No. 16194045.7 dated Feb. 20, 2017.
Rusling, "Enzyme Bioelectrochemistry in Cast Biomembrane-Like Films," Accounts of Chemical Research, 31: 363-369 (1998).
Office Action issued in corresponding European Patent Application No. 16194045.7 dated Aug. 3, 2018.

* cited by examiner

ENZYME ELECTRODE

CROSS-REFERENCE TO RELATED APPLICATION

This application claims the benefit of Japanese Patent Application No. 2015-204033 filed on Oct. 15, 2015 and No. 2016-196930 filed on Oct. 5, 2016 in the Japanese Patent Office, the disclosure of which is herein incorporated in its entirety by reference.

FIELD

The present invention relates to an enzyme electrode for measuring a charge transfer limiting current.

BACKGROUND

An enzyme electrode is known which includes an electrode as a base material and a detection layer, in which an enzyme and electrically conductive particles are immobilized using a crosslinking agent or a binder, on the surface of the electrode. Some enzyme electrodes measure a concentration of an intended substance by measuring a charge transfer limiting current by the electron exchange occurred between an enzyme in the detection layer and the electrode.

Examples of the enzyme electrode which measures a charge transfer limiting current include an enzyme electrode wherein a detection layer contains an enzyme, electrically conductive particles and a crosslinking agent (e.g., Patent document 1). Another enzyme electrode is also known wherein a detection device includes an enzyme, electrically conductive particles and electrically conductive macromolecules (e.g., Patent document 2).

[Patent document 1] Japanese Patent Laid-Open No. 2014-006154

[Patent document 2] Japanese Patent Laid-Open No. 2014-006155

SUMMARY

The enzyme electrode which measures a charge transfer limiting current can suitably measure a concentration of an intended substance in a small amount of a sample. However, the enzyme electrodes disclosed in Patent document 1 and Patent document 2 still need to be improved in the aspects of manufacturing costs and storage stability.

The present invention has an object to provide an enzyme electrode which can reduce the manufacturing costs and improve storage stability.

One of aspects is an enzyme electrode including an electrode, and a detection layer which contacts the electrode and contains a crosslinking agent, an electrically conductive macromolecule and an enzyme transferring and receiving electrons to and from the electrode and does not contain an electron transfer subunit.

In the enzyme electrode, the enzyme may be an oxidoreductase. The enzyme also may be cytochrome dehydrogenase which does not contain an electron transfer subunit.

The aspects include a method of manufacturing an enzyme electrode, including forming, on an electrode, a detection layer which contacts the electrode and contains a crosslinking agent, an electrically conductive macromolecule and an enzyme transferring and receiving electrons to and from the electrode and does not contain an electron transfer subunit.

According to the present invention, it enable to provide an enzyme electrode which can reduce the manufacturing costs and improve storage stability.

DESCRIPTION OF EMBODIMENTS

Hereinafter, the enzyme electrode according to an embodiment of the present invention will be described with reference to the drawings. The configuration of the embodiment described below is illustrative, and the present invention is not limited thereto.

<Configuration of Enzyme Electrode>

Figure 1:
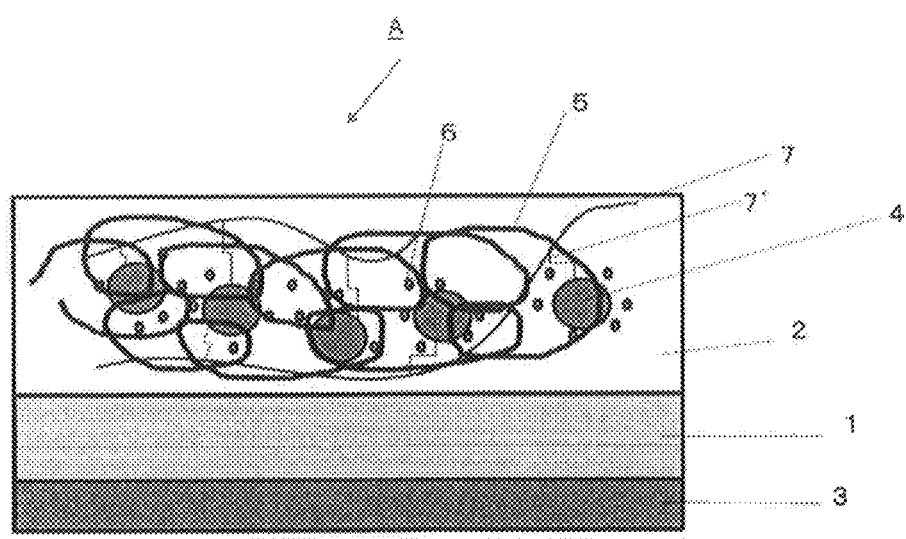
FIG. 1 is a drawing schematically illustrating a configuration of the enzyme electrode according to an embodiment.

FIG. 1 is a drawing schematically illustrating the enzyme electrode according to the embodiment. In FIG. 1, an enzyme electrode A is provided with an electrode 1 and a detection layer 2 formed on the surface (the upper surface in FIG. 1) of the electrode 1.

(Electrode)

The electrode 1 is made of a metallic material such as gold (Au), platinum (Pt), silver (Ag) or palladium, or a carbon material such as carbon. The electrode 1 is formed, for example, on an insulating base plate 3 as illustrated in FIG. 1. The insulating base plate 3 is made of a thermoplastic resin such as polyetherimide (PEI), polyethylene terephthalate (PET) and polyethylene (PE), various resins (plastics) such as polyimide resins and epoxy resins, or insulating materials such as glasses, ceramics and papers. Various known materials are applicable to be the electrode material which forms the electrode 1 and the material for the insulating base plate 3. The size and thickness of the electrode 1 and the insulating base plate 3 can be determined as appropriate. Hereinafter, the combination of the insulating base plate 3 and the electrode 1 is also called "base material".

(Detection Layer)

The detection layer 2 contacts the electrode 1 and contains an enzyme 4, electrically conductive macromolecules 5, a sugar 6 and a crosslinking agent 7, but does not contain an electron mediator. The object to be measured using the enzyme electrode according to the embodiment is a charge transfer limiting current based on the transfer of electrons from the substance to be measured to the electrode. This is an electric current generated when electrons from the enzyme are transferred to the electrode due to the reaction of the enzyme and the substance to be measured, and is a time-independent steady-state current, preferably a steady-state current after the occurrence of the transient current due to the charging of an electric double layer.

For measuring the charge transfer limiting current, the working electrode is preferably a "direct electron transfer-type enzyme electrode". The "direct electron transfer-type enzyme electrode" as used herein refers to a type of an enzyme electrode in which electrons are exchanged between the enzyme and the electrode (namely, an enzyme transfers and receives electrons to and from the electrode) in such a way that electrons generated by an enzyme reaction in a reagent layer are directly, or mediated by electrically conductive macromolecules, transferred to the electrode without the involvement of an oxidation reduction substance such as an electron transfer mediator.

Note that, even when an electron transfer mediator is used, the charge transfer limiting current can be measured in the case where the electron transfer mediator is immobilized so as not to be diffused.

As illustrated in FIG. 1, the molecules of the enzyme 4 within the detection layer 2 are crosslinked by the crosslinking agent 7 and has a complicatedly interwined structure further due to the electrically conductive macromolecule 5. The electrons generated by the enzyme reaction can be transferred to the electrode 1 directly or along the electrically conductive macromolecule 5 having electrical conductivity. Specifically, in the enzyme electrode A according to the embodiment, the electrons are exchanged between the enzyme 4 and the electrode 1 by the direct electron transfer in the detection layer 2.

Note that, in the physiological reaction system, the limiting distance within which the direct electron transfer occurs is considered from 1 to 2 nm, and even in the electron exchange in an electrochemical reaction system consisting of an electrode and an enzyme, the electron exchange on the electrode becomes difficult to detect unless the transfer of a mediator (e.g., transfer by diffusion) is involved in the case where the above distance is farther apart. Consequently, within the detection layer 2, the active sites (the site at which electrons are generated by an enzyme reaction) of the enzyme 4 and the electrically conductive sites of the electrically conductive macromolecule 5 are located within a distance suitable for the electron transfer, specifically, the electrically conductive sites and the active sites are located close enough so that electrons are suitably transferred therebetween.

(Enzyme)

Examples of the enzyme 4 include oxidoreductases. Examples of the oxidoreductase include glucose oxidase (GOD), galactose oxidase, bilirubin oxidase, pyruvic acid oxidase, D- or L-amino acid oxidase, amine oxidase, cholesterol oxidase, choline oxidase, xanthine oxidase, sarcosine oxidase, L-lactic acid oxidase, ascorbic acid oxidase, cytochrome oxidase, alcohol dehydrogenase, glutamate dehydrogenase, cholesterol dehydrogenase, aldehyde dehydrogenase, glucose dehydrogenase (GDH), fructose dehydrogenase, sorbitol dehydrogenase, lactate dehydrogenase, malate dehydrogenase, glycerol dehydrogenase, 17B hydroxysteroid dehydrogenase, estradiol 17B dehydrogenase, amino acid dehydrogenases, glyceraldehyde 3-phosphoric acid dehydrogenase, 3-hydroxysteroid dehydrogenase, diaphorase, cytochrome oxidoreductase, catalase, peroxidase, glutathione reductase and the like. Of these, oxidoreductases of sugars are preferable. Examples of the oxidoreductase of sugars include glucose oxidase (GOD), galactose oxidase, glucose dehydrogenase (GDH), fructose dehydrogenase and sorbitol dehydrogenase.

The oxidoreductase can further contain, as a catalytic subunit and a catalytic domain, at least one of pyrroloquinoline quinone (PQQ) and flavin adenine dinucleotide (FAD). Examples of the oxidoreductase containing PQQ include PQQ glucose dehydrogenase (PQQGDH). Examples of the oxidoreductase containing FAD include cytochrome glucose dehydrogenase (Cy-GDH) and glucose oxidase (GOD), which have an FAD-containing α-subunit.

The oxidoreductase can further contain an electron transfer subunit or an electron transfer domain. Examples of the electron transfer subunit include subunits, which have a heme with the function of electron exchange. Examples of the oxidoreductase containing such a heme-containing subunit include those containing cytochrome, and for example glucose dehydrogenase and a fusion protein of PQQGDH and cytochrome can be used.

Examples of the enzyme containing an electron transfer domain include cholesterol oxidase and quinoheme ethanol dehydrogenase (QHEDH (PQQ Ethanol dh)). For the electron transfer domain, it is further preferable to use domains containing cytochrome, which has a heme with the function of electron exchange. Examples include "QHGDH" (fusion enzyme; GDH with heme domain of QHGDH), sorbitol dehydrogenase (Sorbitol DH), D-fructose dehydrogenase (Fructose DH), *Agrobacterium tumefasience*-derived Glucose-3-Dehydrogenase (G3DH from *Agrobacterium tumefasience*) and cellobiose dehydrogenase. Note that the above fusion protein of PQQGDH and cytochrome, which is the example of the subunit containing cytochrome, and the cytochrome domain of PQQGDH, which is the example of the domain containing cytochrome, are disclosed in, for example, International Publication No. WO2005/030807.

Further, for the oxidoreductase, an oligomer enzyme composed of at least a catalytic subunit and a subunit containing cytochrome having a heme with the function of electron acceptor can be used.

However, an oxidoreductase which does not contain an electron transfer subunit or an electron transfer domain is used as the enzyme in the present embodiment. An example is cytochrome glucose dehydrogenase (Cy-GDH). Cy-GDH has an electron transfer subunit β, a catalytic subunit α and a catalytic subunit γ. In the present embodiment, Cy-GDH which does not have the electron transfer subunit β (contains the catalytic subunits α and γ) is used as the enzyme.

Cy-GDH which does not have the electron transfer subunit β can be purchased at a lower price than Cy-GDH which has the electron transfer subunit β, the catalytic subunit α and the catalytic subunit γ. For this reason, when Cy-GDH which does not have the electron transfer subunit β is used as the enzyme to be contained in the detection layer 2, the manufacturing costs of the enzyme electrode can be reduced.

Cy-GDH which does not have the electron transfer subunit β further has higher stability as the substance than Cy-GDH which has the electron transfer subunit β, the catalytic subunit α and the catalytic subunit γ. This means that the enzyme electrode (biosensor) in which Cy-GDH not having the electron transfer subunit β is used can be stored for a longer period of time than the enzyme electrode (biosensor) in which Cy-GDH having the electron transfer subunit β, the catalytic subunit α and the catalytic subunit γ is used. Consequently, the type of enzyme electrode for a charge transfer limiting measurement, with a longer product life, can be obtained.

(Electrically Conductive Macromolecule (Conductive Polymer))

Examples of the electrically conductive polymer include polypyrrole, polyaniline, polystyrene sulfonate, polythiophene, polyisothianaphthene, polyethylene dioxythiophene (poly(3,4-ethylenedioxythiophene)poly(styrene sulfonate)), the combinations thereof and the like. Examples of the commercial products thereof include, as the polypyrrole, "SSPY" (ethyl 3-methyl-4-pyrrolecarboxylate) (manufactured by KAKENSANGYOU CORPORATION) and the like. Examples also include, as the polyaniline, "AquaPASS 01-x" (manufactured by TA Chemical Co., Ltd.) and the like.

Examples further include, as the polystyrene sulfonate, "Poly-NaSS" (manufactured by TOSOH ORGANIC CHEMICAL CO., LTD.) and the like. Examples include, as the polythiophene, "ESPACER 100" (manufactured by TA Chemical Co., Ltd.) and the like. Examples include, as the polyisothianaphthene, "ESPACER 300" (manufactured by TA Chemical Co., Ltd.) and the like. Examples include, as the polyethylene dioxythiophene (poly(3,4-ethylenedioxythiophene)poly(styrene sulfonate)), "PEDOT-PSS" (Polyscience, Inc.) and the like.

Additionally, electrically conductive polymers with various properties (e.g., water solubility) can be used. Functional groups of the electrically conductive polymers preferably have a hydroxy group or a sulfo group.

(Sugar)

The detection layer 2 can contain the sugar 6, as illustrated in FIG. 1, in addition to the enzyme, the crosslinking agent and the electrically conductive macromolecule. The sugar 6 is a sugar which does not serve as a substrate for the enzyme 4, and the number of constituent sugar of the sugar 6 is, for example, 1 to 6, and preferably 2 to 6. These may be a D-form or an L-form, or a mixture thereof, and can be used singly or two or more thereof can be used in combination as appropriate. However, in the case where a sugar such as glucose is used as a measurement object, a sugar which is different from the sugar of the measurement object and which does not serve as a substrate for the enzyme 4 is used as the sugar 6.

Examples of the disaccharide include xylobiose, agarobiose, carrabiose, maltose, isomaltose, sophorose, cellobiose, trehalose, neotrehalose, isotrehalose, inulobiose, vicianose, isoprimeverose, sambubiose, primeverose, solabiose, melibiose, lactose, lycobiose, epicellobiose, sucrose, turanose, maltulose, lactulose, epigentibiose, robinobiose, silanobiose, rutinose and the like. Examples of the trisaccharide include glucosyl trehalose, cellotriose, chacotriose, gentianose, isomaltotriose, isopanose, maltotriose, manninotriose, melezitose, panose, planteose, raffinose, soratriose, umbelliferose and the like.

Examples of tetrasaccharides include maltosyl trehalose, maltotetraose, stachyose and the like. Examples of the pentasaccharides include maltotriosyl trehalose, maltopentaose, verbascose and the like. Examples of the hexasaccharide include maltohexaose and the like.

(Crosslinking Agent)

Examples of the type of crosslinking agent 7 include, specifically as the aldehyde group-containing compound, glutaraldehyde, formaldehyde, malonaldehyde, terephthalaldehyde, isobutyraldehyde, valeraldehyde, isovaleraldehyde, cinnamaldehyde, nicotinaldehyde, glyceraldehyde, glycoaldehyde, succinaldehyde, adipaldehyde, isophthalaldehyde, terephthalaldehyde and the like. Examples include, as the carbodiimide group-containing compound, hexamethylene diisocyanate, hydrogenated xylylene diisocyanate, xylylene diisocyanate, 2,2,4-trimethylhexamethylene diisocyanate, 1,12-diisocyanate dodecane, norbornane diisocyanate, 2,4-bis-(8-isocyanateoctyl)-1,3-dioctylcyclobutane, 4,4'-dicyclohexylmethane diisocyanate, tetramethylxylylene diisocyanate, isophorone diisocyanate and the like. The carbodiimide group-containing compounds are also commercially available under the names of CARBODILITE V-02, CARBODILITE V-02-L2, CARBODILITE V-04, CARBODILITE V-06, CARBODILITE E-02, CARBODILITE V-01, CARBODILITE V-03, CARBODILITE V-05, CARBODILITE V-07, CARBODILITE V-09 (all are product names, manufactured by Nisshinbo Chemical Inc.) and the like.

Examples include, as the maleimide group-containing compound, m-maleimidobenzoyl-N-hydroxysuccinimide ester, sulfonsuccinimidyl 4-(p-maleimidophenyl)butyrate, m-maleimidobenzoyl sulfosuccinimide ester, N-γ-maleimidobutyryloxysuccinimide ester, succinimidyl 4-(N-maleidomethyl)cyclohexane 1-carboxylate, N-succinimidyl-2-maleimidoacetic acid, N-succinimidyl-4-maleimidobutyric acid, N-succinimidyl-6-maleimidohexanoic acid, N-succinimidyl-4-maleimidomethylcyclohexane-1-carboxylic acid, N-sulfosuccinimidyl-4-maleimidomethylcyclohexane-1-carboxyl is acid, N-succinimidyl-4-maleimidomethylbenzoate, N-succinimidyl-3-maleimidobenzoate, N-succinimidyl-4-maleimidophenyl-4-butyric acid, N-sulfosuccinimidyl-4-maleimidophenyl-4-butyric acid, N,N'-oxydimethylene-dimaleimide, N,N'-o-phenylene-dimaleimide, N,N'-m-phenylene-dimaleimide, N,N'-p-phenylene-dimaleimide, N,N'-hexamethylene-dimaleimide, N-succinimidyl maleimide carboxylate and the like. Examples also include commercial products such as SANFEL BM-G (manufactured by SANSHIN CHEMICAL INDUSTRY CO., LTD.) and the like.

Examples include, as the oxazoline group-containing compound, oxazoline compounds such as 2,2'-bis-(2-oxazoline), 2,2'-methylene-bis-(2-oxazoline), 2,2'-ethylene-bis-(2-oxazoline), 2,2'-trimethylene-bis-(2-oxazoline), 2,2'-tetramethylene-bis-(2-oxazoline), 2,2'-hexamethylene-bis-(2-oxazoline), 2,2'-octamethylene-bis-(2-oxazoline), 2,2'-ethylene-bis-(4,4'-dimethyl-2-oxazoline), 2,2'-p-phenylene-bis-(2-oxazoline), 2,2'-m-phenylene-bis-(2-oxazoline), 2,2'-m-phenylene-bis-(4,4'-dimethyl-2-oxazoline), bis-(2-oxazolinylcyclohexane) sulfide, bis-(2-oxazolinylnorbornane) sulfide and the like.

Examples include, as the addition polymerizable oxazoline compound, 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl-2-oxazoline, 2-isopropenyl-5-ethyl-2-oxazoline and the like, and polymerized or copolymerized compounds of one or more thereof can be used.

The oxazoline group-containing compounds are also commercially available under the names of EPOCROS WS-500, EPOCROS WS-700, EPOCROS K-1010E, EPOCROS K-1020E, EPOCROS K-1030E, EPOCROS K-2010E, EPOCROS K-2020E, EPOCROS K-2030E, EPOCROS RPS-1005, EPOCROS RAS-1005 (all manufactured by NIPPON SHOKUBAI CO., LTD.), NK Linker FX (manufactured by Shin-Nakamura Chemical Co., Ltd.) and the like.

Examples specifically include, as the epoxy group-containing compound, sorbitol polyglycidyl ether, polyglycerol polyglycidyl ether, diglycerol polyglycidyl ether, glycerol polyglycidyl ether, trimethylolpropane polyglycidyl ether, ethylene glycol diglycidyl ether, polyethylene glycol diglycidyl ether, propylene glycol diglycidyl ether, polypropylene glycol diglycidyl ether and the like, and two or more of these compounds can also be used in combination. The epoxy group-containing compounds are also commercially available under the names of Denacol EX-611, Denacol EX-612, Denacol EX-614, Denacol EX-614B, Denacol EX-512, Denacol EX-521, Denacol EX-421, Denacol EX-313, Denacol EX-314, Denacol EX-321, Denacol EX-810, Denacol EX-811, Denacol EX-850, Denacol EX-851, Denacol EX-821, Denacol EX-830, Denacol EX-832, Denacol EX-841, Denacol EX-861, Denacol EX-911, Denacol EX-941, Denacol EX-920, Denacol EX-145 and Denacol EX-171 (all are product names, manufactured by Nagase ChemteX Corporation), SR-PG, SR-2EG, SR-8EG, SR-8EGS, SR-GLG, SR-DGE, SR-4GL, SR-4GLS and SR-SEP (all are product names, manufactured by Sakamoto Yakuhin Kogyo Co., Ltd.), Epolite 200E, Epolite 400E, Epolite 400P (all are manufactured by KYOEISHA CHEMICAL Co., LTD.) and the like.

The type of crosslinking agent is not limited to the above compounds and commercial products but may be any compounds containing at least one functional group of an aldehyde group, a maleimide group, a carbodiimide group, an oxazoline group and an epoxy group. The form of crosslinking agent is not limited and may be in the form of a monomer or a polymer.

(Electrically Conductive Particles)

The detection layer 2 can further contain electrically conductive particles. For the electrically conductive particles, metal particles such as gold, platinum, silver or palladium, or higher-order structures made of a carbon material, can be used. The higher-order structure can contain, for example, electrically conductive carbon black, carbon nanotube (CNT) and carbon particles or carbon fine particles such as fullerene. Examples of the electrically conductive carbon black include Ketjenblack (manufactured by Degussa AG), BLACK PEARL (Cabot Corporation) and the like.

Note that the surface of the detection layer 2 may also be covered with an outer layer film such as cellulose acetate. Examples of the raw material for the outer layer film include, among others, polyurethane, polycarbonate, polymethylmethacrylate, butylmethacrylate, polypropylene, polyether ether ketone and the like.

(Method of Producing Enzyme Electrode)

The above enzyme electrode A is, for example, produced as follows. Specifically, a metal layer which functions as the electrode 1 is formed on one surface of the insulating base plate 3. For example, a metal layer having a desired thickness (e.g., about 30 nm) can be formed on one surface of the insulating base plate 3 in the shape of film having a predetermined thickness (e.g., about 100 μm) by forming a film by depositing a metallic material by physical vapor deposition (PVD, e.g., sputtering) or chemical vapor deposition (CVD). Instead of the metal layer, an electrode layer made of a carbon material can also be formed.

Next, the detection layer 2 is formed on the electrode 1. Specifically, a solution (reagent) containing the enzyme 4, the electrically conductive macromolecule 5, the sugar 6 and the crosslinking agent 7 is prepared. The concentration of the sugar herein is preferably from 0.1 to 2 wt %, and more preferably 0.2 to 2 wt %. The solution (reagent) is dropped onto the surface of the electrode 1. When the solution (reagent) is solidified by drying on the electrode 1, the enzyme electrode A, wherein the detection layer 2 is formed on the electrode 1, is obtained.

The use of the enzyme electrode according to the embodiment enables the concentration measurement of a substance to be tested in a sample based on a charge transfer limiting current. The substance to be measured as referred herein is not limited as long as the substance is measurable by the measurement method using the enzyme electrode of the present invention, but is preferably a substance of a biological origin and can be an indicator for a disease or health conditions with examples including glucose, cholesterol and the like. The sample is not limited as long as it contains the substance to be measured but is preferably a biological sample with examples including blood, urine and the like.

(Biosensor)

The enzyme electrode according to the embodiment can be used as a biosensor such as a glucose sensor. The biosensor includes, together with the enzyme electrode, an electrode to be the counter electrode. The counter electrode may be any electrode which can be commonly used as the counter electrode of the biosensor, and, for example, a carbon electrode obtained by forming a film using screen printing, a metal electrode obtained by forming a film using physical vapor deposition (PVD, e.g., sputtering) or chemical vapor deposition (CVD) and a silver/silver chloride electrode obtained by forming a film using screen printing can be used. A three-electrode system may also be used in which a reference electrode is the silver/chloride silver electrode, the carbon electrode obtained by forming a film using screen printing or the metal electrode obtained by forming a film using physical vapor deposition (PVD, e.g., sputtering) or chemical vapor deposition (CVD).

(Measuring Apparatus)

Next, the measuring apparatus for measuring a concentration of the substance using the enzyme electrode according to the embodiment is described. A glucose measuring apparatus using a glucose sensor, which is an example of the biosensor which uses the enzyme electrode, is illustrated here. However, the measuring apparatus is not limited to the glucose measuring apparatus, and the purpose of use of the measuring apparatus changes depending on the substance to be measured by the enzyme electrode (biosensor).

Figure 2:
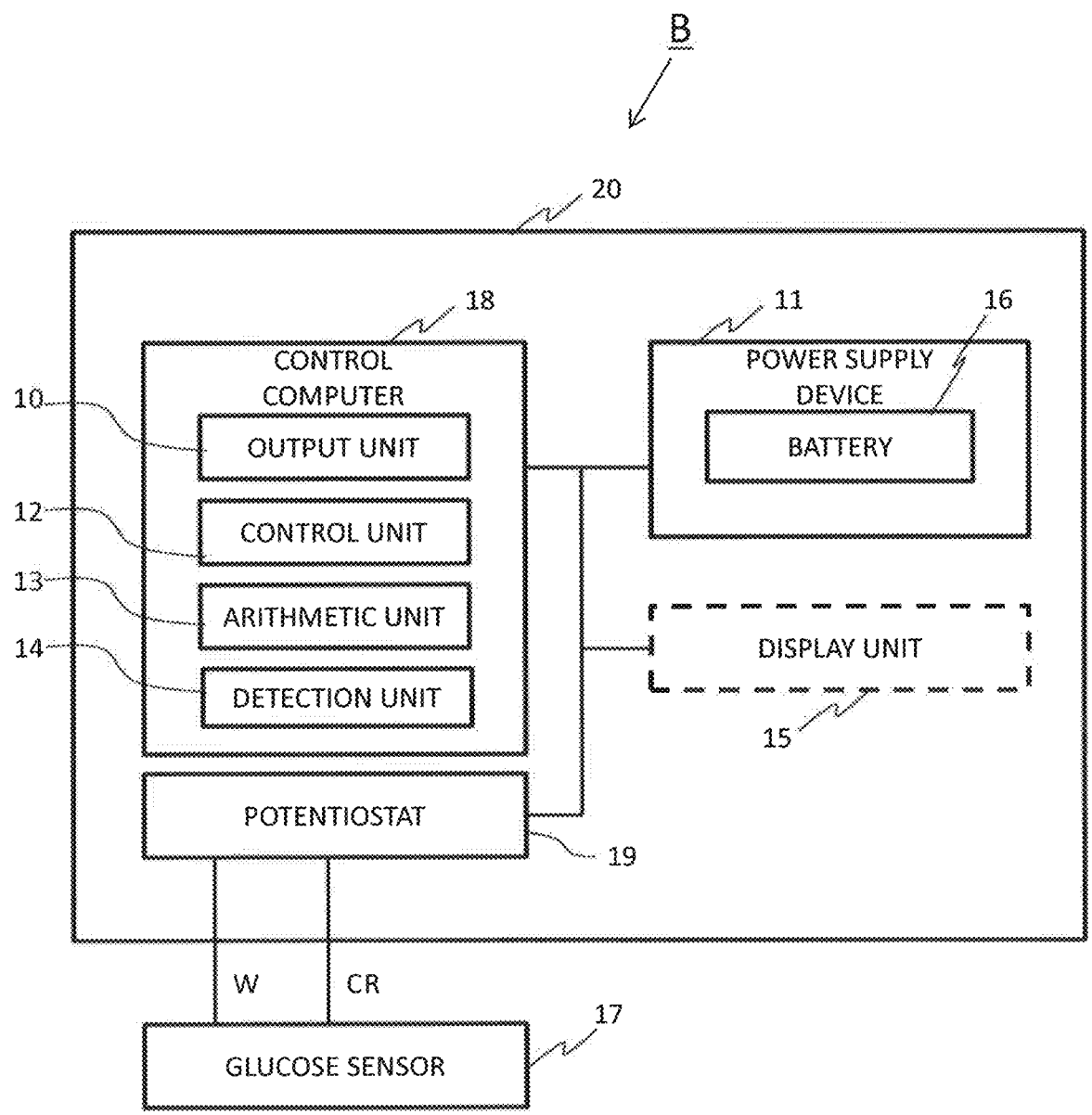
FIG. 2 is a schematic drawing illustrating an embodiment of the measuring apparatus of the present invention.

FIG. 2 illustrates an example of the configuration of main electronic components housed in the measuring apparatus B. A control computer 18, a potentiostat 19 and a power supply device 11 are provided on a base plate 20 housed in a housing. The control computer 18 includes, as hardware, a processor such as CPU (Central Processing Unit), recording media such as memories (RAM (Random Access Memory) and ROM (Read Only Memory)) and the communication unit.

When the processor loads a program stored in the recording medium (e.g., ROM) to the RAM and executes the program, the control computer 18 functions as an apparatus including an output unit 10, a control unit 12, an arithmetic unit 13 and a detection unit 14. The control computer 18 may also include an auxiliary memory such as a semiconductor memory (EEPROM or flash memory) or a hard disk for storing programs and data.

The control unit 12 controls the timing for applying the voltage, the value of the voltage to be applied and the like. The power supply device 11 includes a battery 16, and supplies electricity to the control computer 18 and the potentiostat 19 for operation. It is also possible to dispose the power supply device 11 outside the housing.

The potentiostat 19 is a device which maintains the potential of the working electrode constant with respect to the reference electrode and is controlled by the control unit 12. The potentiostat 19 applies a predetermined amount of voltage between the counter electrode and the working electrode of the glucose sensor 17 using terminals CR, W, measures the response electric current of the working electrode which can be obtained at the terminal W, and sends the measurement results of the response electric current to the detection unit 14.

The arithmetic unit 13 calculates and stores the concentration of the substance to be measured based on the value of the detected electric current. The output unit 10 carries out data communication with the display unit 15 and sends the calculated result of the concentration of the substance to be measured, which is provided by the arithmetic unit 13, to the display unit 15. The display unit 15 is capable of displaying, for example, the calculated result of the glucose concentration received from the measuring apparatus B, on a display screen in a predetermined format.

Figure 3:
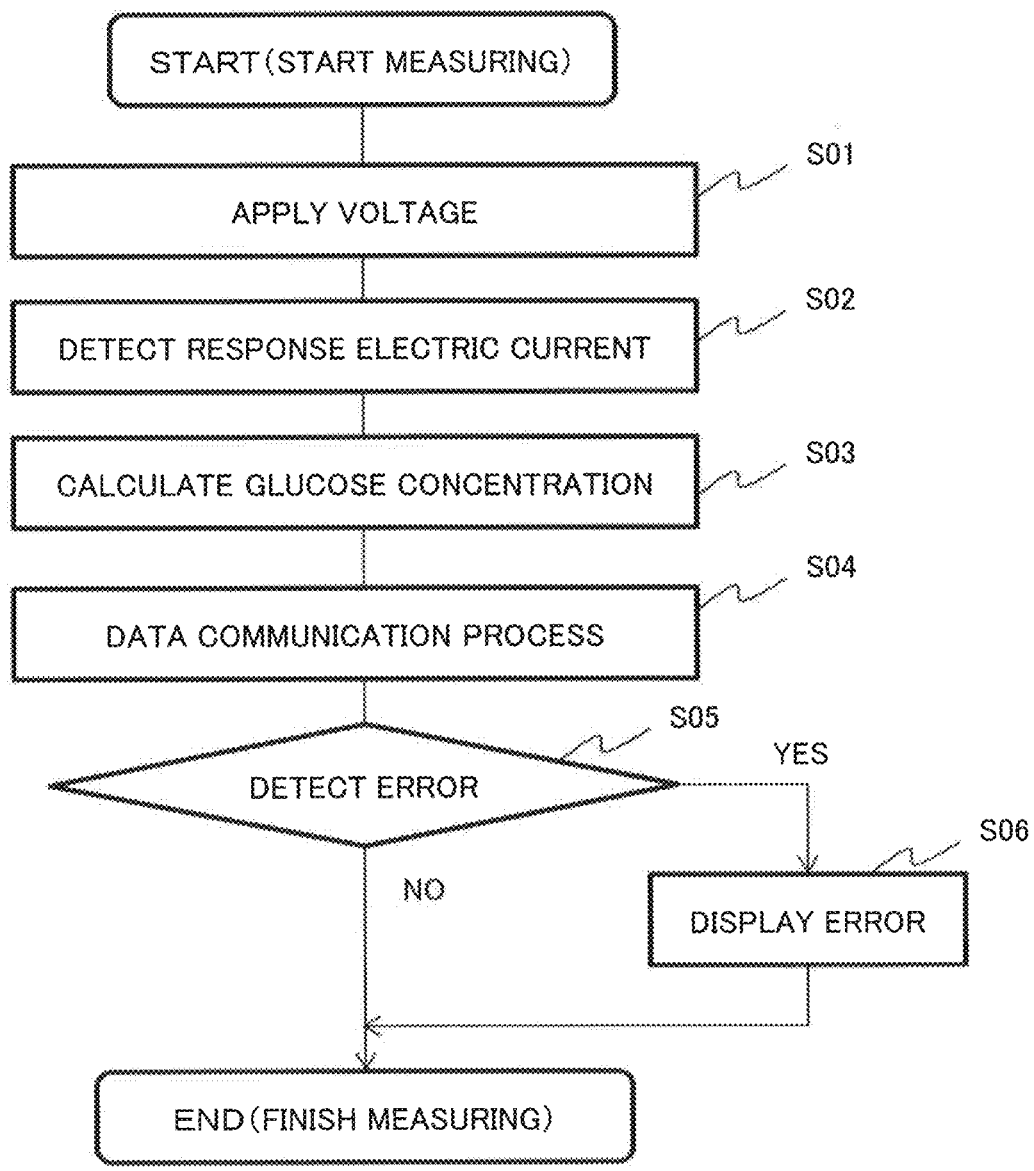
FIG. 3 is a flow chart illustrating an embodiment of a measurement program using the measuring apparatus of the present invention.

FIG. 3 is a flow chart illustrating an example of the processing sequence of the glucose concentration measurement carried out by the control computer 18. The CPU (control unit 12) of the control computer 18 receives an instruction to start the measurement of the glucose concentration. The control unit 12 controls the potentiostat 19 to apply a predetermined amount of voltage to the working electrode, and starts measuring the response electric current from the working electrode (Step S01). Note that the detection of the installation of the glucose sensor 17 to the measuring apparatus B may be used as the instruction to start the concentration measurement.

Next, the potentiostat 19 measures the response electric current generated by the application of voltage, specifically, the charge transfer limiting current based on the transfer to the electrode of electrons derived from the substance to be measured (glucose, herein) in the sample, and sends the measured current to the detection unit 14 (Step S02). As the charge transfer limiting current, the steady-state current after the occurrence of the transient current due to the charging of an electric double layer, for example, 1 to 20 seconds after the application of voltage, is measured.

The arithmetic unit 13 carried out arithmetic processing based on the electric current value and calculates the glucose concentration (Step S03). For example, the formulae for calculating the glucose concentration or the data of the calibration curve of the glucose concentration, which correspond to an enzyme (e.g., glucose dehydrogenase) contained in the detection layer disposed on the working electrode, are preinstalled to the arithmetic unit 13 in the control computer 18. The arithmetic unit 13 calculates the glucose concentration using these calculation formulae or the calibration curve.

The output unit 10 sends the calculated result of the glucose concentration to the display unit 15, through a communication link provided with the display unit 15 (Step S04). Thereafter, the control unit 12 determines if there are any measurement errors detected (Step S05), completes the measurement if there is no error and displays the glucose concentration on the display unit. If there are any errors, a notification of error is displayed, and then the flow sequence illustrated in FIG. 3 is completed. The calculation result may be stored in a storage medium and read out the calculation result from the storage medium to display and confirm. Note that the detection of measurement error by the control unit 12 (Step S05) is carried out after the calculated result is sent to the display unit 15 (Step S04) in the example of FIG. 3, but it is also possible to carry out these steps in switching orders.

EXAMPLE

Hereinafter, Examples of the enzyme electrode are described.
(Test 1)
(Preparation of Reagent Solution)
Two types of reagent solutions according to Example 1 and Comparative Example 1 as described below were prepared.

Example 1

(Formulation)
Ketjenblack (Mitsubishi Carbon Black) 0.6%
Electrically conductive macromolecule: sulfonated polyaniline aqueous solution (tradename: aquaPASS-01x, manufactured by Mitsubishi Rayon Co., Ltd.): 0.2%
Oxazoline group-containing polymer EPOCROS WS-700 (NIPPON SHOKUBAI CO., LTD.): 3.0%
Enzyme (Cy-GDH: $\gamma\alpha$): 2.5 mg/mL
Trehalose: 0.25% (protection agent of the enzyme)
Phosphate buffer solution: (pH 5.8): 5 mM
Note that "%" represents the percent by weight concentration of the reagent contained in the reagent solution.

Comparative Example 1

(Formulation)
Ketjenblack (Mitsubishi Carbon Black): 0.6%
Electrically conductive macromolecule: sulfonated polyaniline aqueous solution (tradename: aquaPASS-01x, manufactured by Mitsubishi Rayon Co., Ltd.): 0.2%
Oxazoline group-containing polymer EPOCROS WS-700 (NIPPON SHOKUBAI CO., LTD.): 3.0%
Enzyme (Cy-GDH: $\gamma\alpha\beta$): 2.3 mg/mL
Trehalose: 0.25% (protection agent of the enzyme)
Phosphate buffer solution: (pH 5.8): 5 mM
Note that "%" represents the percent by weight concentration of the reagent contained in the reagent solution. Thus, the reagent solution of Comparative Example 1 is different in the aspect that Cy-GDH having the subunits $\alpha$, $\beta$ and $\gamma$ are used as the enzyme from the reagent solution of Example 1 which uses Cy-GDH having the subunits $\alpha$ and $\gamma$.

(Production of Enzyme Electrode (Sample))

Next, a plurality of insulating base plates having on one surface thereof an electrode (electrode layer) formed by gold vapor deposition (base material) were prepared, and the reagent solution according to Example 1 or Comparative Example 1 was dispensed on each of the insulating base plates, allowed to stand for 30 minutes in a low humidity drying furnace and dried. Thus, the enzyme electrodes (samples) according to Example 1 and the enzyme electrodes (samples) according to Comparative Example 1, on which the detection layers were formed when the reagents were solidified on the electrodes, were obtained.

(Measurement of Glucose Concentration)

Next, the response electric current value was measured for human whole bloods in which the concentration of glucose was adjusted respectively to 0, 100 mg/dL, 300 mg/dL, 600 mg/dL and 800 mg/dL, using each of the enzyme electrodes. Glucose was measured using a reference electrode/counter electrode (both made of carbon) and a reference electrode (silver/silver chloride) formed on the electrode, with a voltage of +200 mV applied to the working electrode (vs. Ag/AgCl).

(Evaluation of Measurement Results)

Figure 4:
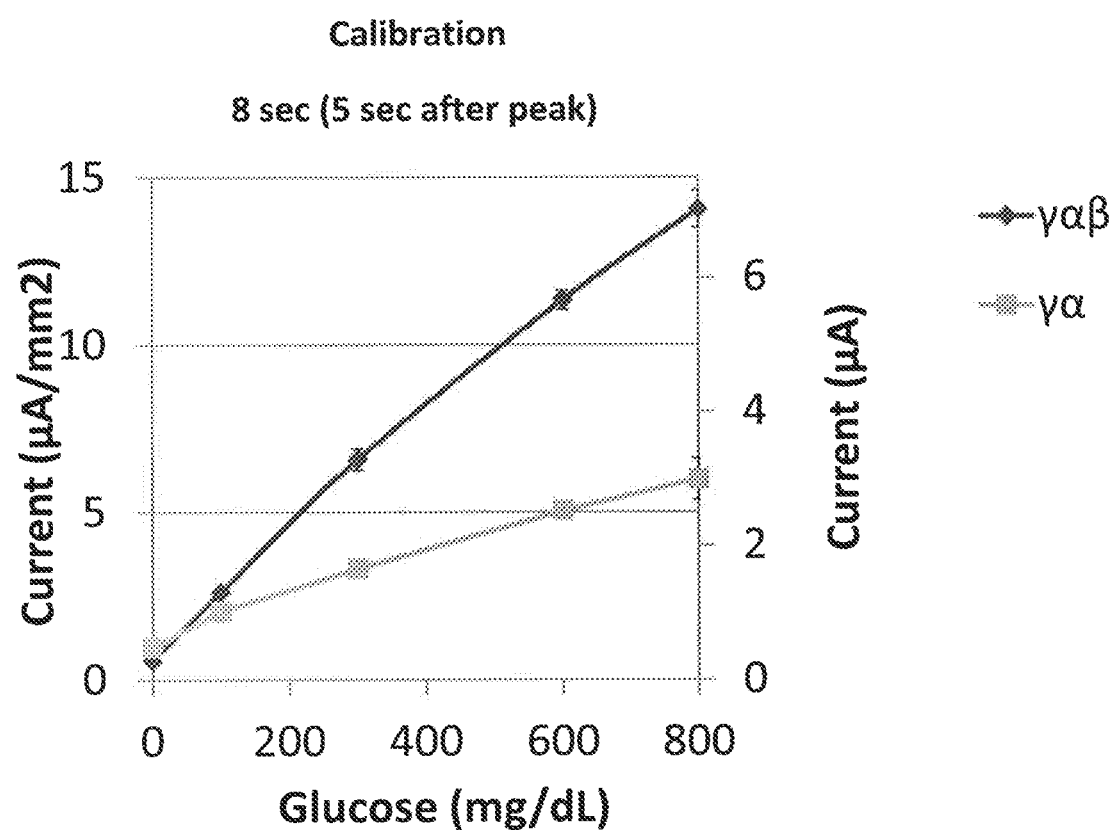
FIG. 4 is a graph depicting comparisons of the calibration curves created based on response electric current values obtained using the enzyme electrodes of Example 1 and Comparative Example 1.

FIG. 4 is a graph depicting comparisons of the calibration curves created based on response electric current values obtained using the enzyme electrodes of Example 1 and Comparative Example 1. As depicted in FIG. 4, it is revealed that the $\gamma\alpha$ (Example 1) is suggested, with the linear range of the calibration, to be sufficiently used as a glucose sensor although the response electric current values are lower than the $\gamma\alpha\beta$ (Comparative Example 1). According to Test 1, the enzyme electrode, with reduced manufacturing costs and improved quality stability of the detection layer 2, can be thus provided.

The enzyme electrode according to Example 1 measures a charge transfer limiting current, due to which inconsistencies of measured values caused by diffusion conditions of a substance, as occurred with the conventional enzyme electrodes which use a mediator, can be obviated. As described above, the enzyme electrode according to the embodiment can provide the enzyme electrode, with improved storage stability at a lower price, which enables more quantitative measurement (measurement accuracy is high) than the enzyme electrode which uses a mediator.

What it claimed is:

1. A direct electron transfer-type enzyme electrode comprising:
   an electrode; and
   a detection layer which contacts the electrode and contains an oxazoline group-containing compound, trehalose, an electrically conductive macromolecule and an enzyme transferring and receiving electrons to and from the electrode, wherein said detection layer does not contain an electron mediator,
   wherein said enzyme is cytochrome glucose dehydrogenase which does not contain an electron transfer subunit, and
   wherein said electrically conductive macromolecule is selected from the group consisting of polypyrrole, polystyrene sulfonate, polythiophene, polyisothianaphthene, polyethylene dioxythiophene(poly(3,4-ethylenedioxythiophene)poly(styrenesulfonate)), and the combinations thereof.

2. The direct electron transfer-type enzyme electrode according to claim 1, wherein said detection layer further contains electrically conductive particles.

3. The direct electron transfer-type enzyme electrode according to claim 1, wherein said electrically conductive macromolecule is polypyrrole.

4. The direct electron transfer-type enzyme electrode according to claim 1, wherein said electrically conductive macromolecule comprises polystyrene sulfonate.

5. The direct electron transfer-type enzyme electrode according to claim 1, wherein said electrically conductive macromolecule comprises polythiophene.

6. The direct electron transfer-type enzyme electrode according to claim 1, wherein said electrically conductive macromolecule comprises polyisothianaphthene.

7. The direct electron transfer-type enzyme electrode according to claim 1, wherein said electrically conductive macromolecule comprises polyethylene dioxythiophene (poly(3,4-ethylenedioxythiophene)poly(styrene sulfonate)).

8. The direct electron transfer-type enzyme electrode according to claim 1, wherein the oxazoline group-containing compound comprises one selected from the group consisting of 2,2'-bis-(2-oxazoline),2,2'-methylene-bis-(2-oxazoline), 2,2'-ethylene-bis-(2-oxazoline),2,2'-trimethylene-bis-(2-oxazoline),2,2'-tetramethylene-bis-(2-oxazoline),2,2'-hexamethylene-bis-(2-oxazoline),2,2'-octamethylene-bis-(2-oxazoline),2,2'-ethylene-bis-(4,4'-dimethyl-2-oxazoline),2,2'-p-phenylene-bis-(2-oxazoline), 2,2'-m-phenylene-bis-(2-oxazoline),2,2'-m-phenylene-bis-(4,4'-dimethyl-2-oxazoline),bis-(2-oxazolinylcyclohexane) sulfide, and bis-(2-oxazolinylnorbornane)sulfide.

9. The direct electron transfer-type enzyme electrode according to claim 1, wherein the oxazoline group-containing compound comprises polymerizable oxazoline compound selected from the group consisting of 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl-2-oxazoline, 2-isopropenyl-5-ethyl-2-oxazoline, and polymerized or copolymerized compounds of one or more thereof.

10. A method of manufacturing a direct electron transfer-type enzyme electrode, comprising:
    forming, on an electrode, a detection layer which contacts the electrode and contains an oxazoline group-containing compound-, trehalose, an electrically conductive macromolecule and an enzyme transferring, wherein said detection layer does not contain an electron mediator, and
    receiving electrons to and from the electrode,
    wherein said enzyme is cytochrome glucose dehydrogenase and does not contain an electron transfer subunit, and
    wherein said electrically conductive macromolecule is selected from the group consisting of polypyrrole, polystyrene sulfonate, polythiophene, polyisothianaphthene, polyethylene dioxythiophene(poly(3,4-ethylenedioxythiophene)poly(styrenesulfonate)), and the combinations thereof.

11. The method according to claim 10, wherein said detection layer further contains electrically conductive particles.

12. The direct electron transfer-type enzyme electrode according to claim 10, wherein said electrically conductive macromolecule comprises polystyrene sulfonate.

13. The direct electron transfer-type enzyme electrode according to claim 10, wherein said electrically conductive macromolecule comprises polythiophene.

14. The direct electron transfer-type enzyme electrode according to claim 10, wherein said electrically conductive macromolecule comprises polyisothianaphthene.

15. The direct electron transfer-type enzyme electrode according to claim 10, wherein said electrically conductive macromolecule comprises polyethylene dioxythiophene (poly(3,4-ethylenedioxythiophene)poly(styrenesulfonate)).

16. The direct electron transfer-type enzyme electrode according to claim 10, wherein the oxazoline group-containing compound comprises one selected from the group consisting of 2,2'-bis-(2-oxazoline), 2,2'-methylene-bis-(2-oxazoline), 2,2'-ethylene-bis-(2-oxazoline),2,2'-trimethylene-bis-(2-oxazoline),2,2'-tetramethylene-bis-(2-oxazoline),2,2'-hexamethylene-bis-(2-oxazoline),2,2'-octamethylene-bis-(2-oxazoline),2,2'-ethylene-bis-(4,4'-dimethyl-2-oxazoline),2,2'-p-phenylene-bis-(2-oxazoline), 2,2'-m-phenylene-bis-(2-oxazoline),2,2'-m-phenylene-bis-(4,4'-dimethyl-2-oxazoline),bis-(2-oxazolinylcyclohexane) sulfide, and bis-(2-oxazolinylnorbornane)sulfide.

17. The direct electron transfer-type enzyme electrode according to claim 10, wherein the oxazoline group-containing compound comprises polymerizable oxazoline compound selected from the group consisting of 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl-2-oxazoline, 2-isopropenyl-5-ethyl-2-oxazoline, and polymerized or copolymerized compounds of one or more thereof.

18. A direct electron transfer-type enzyme electrode comprising:
    an electrode; and
    a detection layer which contacts the electrode and contains a crosslinking agent, trehalose, an electrically conductive macromolecule and an enzyme transferring and receiving electrons to and from the electrode, wherein said detection layer does not contain an electron mediator,
    wherein said enzyme is cytochrome glucose dehydrogenase which does not contain an electron transfer subunit,
    wherein said crosslinking agent is selected from the group consisting of aldehyde group-containing compounds, maleimide group-containing compounds, oxazoline group-containing compounds, and epoxy group-containing compounds, and wherein said electrically conductive macromolecule is selected from the group consisting of polypyrrole, polyaniline, polystyrene sulfonate, polythiophene, polyisothianaphthene, polyethylene dioxythiophene (poly(3,4-ethylenedioxythiophene)poly(styrenesulfonate)), and the combinations thereof.

19. The direct electron transfer-type enzyme electrode according to claim 18, wherein said detection layer further contains electrically conductive particles.

* * * * *